(12) United States Patent
Andersch et al.

(10) Patent No.: US 8,426,605 B2
(45) Date of Patent: Apr. 23, 2013

(54) ACTIVE SUBSTANCE COMBINATIONS THAT HAVE NEMATICIDAL, INSECTICIDAL, AND FUNGICIDAL PROPERTIES AND ARE BASED ON TRIFLUOROBUTENYL COMPOUNDS

(75) Inventors: Wolfram Andersch, Bergisch Gladbach (DE); Ulrike Wachendorff-Neumann, Neuwied (DE); Anton Kraus, Leichlingen (DE)

(73) Assignee: Makhteshim Chemical Works, Ltd. (IL)

( * ) Notice: Subject to any disclaimer, the term of this patent is extended or adjusted under 35 U.S.C. 154(b) by 678 days.

(21) Appl. No.: 10/555,106

(22) PCT Filed: Apr. 20, 2004

(86) PCT No.: PCT/EP2004/004165
§ 371 (c)(1),
(2), (4) Date: Dec. 28, 2006

(87) PCT Pub. No.: WO2004/095929
PCT Pub. Date: Nov. 11, 2004

(65) Prior Publication Data
US 2007/0155706 A1     Jul. 5, 2007

(30) Foreign Application Priority Data
May 2, 2003   (DE) .................... 103 19 591

(51) Int. Cl.
C07D 277/36    (2006.01)
A01N 43/78     (2006.01)

(52) U.S. Cl.
USPC ..................................... 548/182; 504/266

(58) Field of Classification Search ............ 514/369
See application file for complete search history.

(56) References Cited

U.S. PATENT DOCUMENTS

| | | | |
|---|---|---|---|
| 2,758,115 | A | 8/1956 | Lorenz |
| 3,058,990 | A | 10/1962 | Harman |
| 3,264,177 | A | 8/1966 | Kenaga |
| 3,309,266 | A | 3/1967 | Magee |
| 3,513,172 | A | 5/1970 | Brokke |
| 4,748,186 | A | 5/1988 | Cullen et al. |
| 6,277,791 | B1 | 8/2001 | Assmann et al. |
| 6,734,198 | B1 * | 5/2004 | Watanabe et al. ............ 514/369 |
| 6,743,814 | B2 | 6/2004 | Wantanabe et al. |
| 7,078,527 | B2 | 7/2006 | Straub |
| 7,385,093 | B2 | 6/2008 | Straub |
| 7,439,408 | B2 | 10/2008 | Straub |
| 2004/0192672 | A1 * | 9/2004 | Wegmann et al. ....... 514/217.03 |
| 2006/0004196 | A1 | 1/2006 | Straub |
| 2006/0173190 | A1 | 8/2006 | Watanabe et al. |
| 2007/0155680 | A1 | 7/2007 | Andersch et al. |

FOREIGN PATENT DOCUMENTS

| | | |
|---|---|---|
| AU | 2004233565 A1 | 11/2004 |
| DE | 26 41 343 A1 | 4/1977 |
| EP | 0 210 487 A1 | 2/1987 |
| EP | 0 234 045 A2 | 9/1987 |
| EP | 0 347 488 A1 | 12/1989 |
| GB | 1181657 | 2/1970 |
| WO | 8607590 A1 | 12/1986 |
| WO | WO 93/10083 | 5/1993 |
| WO | WO 93/22297 | 11/1993 |
| WO | 9524403 A1 | 9/1995 |
| WO | WO 01/02378 A1 | 1/2001 |
| WO | WO 03/029231 A1 | 4/2003 |
| WO | 03059896 A1 | 7/2003 |
| WO | 2004005268 A1 | 1/2004 |
| WO | 2004095930 A1 | 11/2004 |
| WO | 2005003107 A1 | 1/2005 |
| WO | 2007089455 A1 | 8/2007 |

OTHER PUBLICATIONS

Dialog Database, Accession No. 1284894, English language abstract for DE 26 41 343 A1.
Dialog Database, Accession No. 3940248, English language abstract for EP 0 210 487 A1.
K.H. Buchel., "Pflanzenschutz und Schadlingsbekampfung" [Crop protection and pest control], Georg Thieme Verlag, Stuttgart, pp. 87, 136, 141, 146-153 (1977).
FRAC Code List ©: Fungicides sorted by mode of action (2009).
Tolylfluanid and Dichlofluanid, The e-Pesticide Manual (14 edn.) ver 4.0 (2006).
Yuji Oka, et al, "Nematicidal efficacy of MCW-2, a new nematicide of the fluoroalkenyl group, against the root-knot nematode *Meloidogyne javanica*" Pest Manag Sci 65; 1082-1089 (2009).
S.R. Colby, Calculating Synergistic and Antagonistic Responses of Herbicide Combinations, Weeds, 1967, pp. 20-22.
The Carlton Savings Co. Ltd., re Appl. No. AU 20,769/67; Comm'r Patents, vol. 34, No. 14, p. 1404 (Australia).
AU Official Action issued on Apr. 22, 2008 (AU App. No. 2004233565).
The Carlton Savings Co. Ltd., re Appl. No. AU 20,769/67; Comm'r Patents, vol. 34, No. 14, p. 1404 (Australia), (1973).
Beecham Group Ltd's (Amoxycillin) Application, Ct. of Appl. AU, 1980 R.P.C. No. 10 (1980) pp. 261-304.
In re I.G. Farbenindustrie A.G.'s Patents, High Court Just. (Chancery Div.) vol. XLVII, No. 9, (1930) pp. 389-334.
E.I. Du Pont de Nemours & Co. (Witsiepe) Application, House of Lords, Fleet Street Reports (1982), pp. 303-316.
Examiner report in corresponding AU Application No. 2004233565, Jun. 2, 2009.
Office action issued by the Canadian Patent Office in connection with the corresponding case CA 2524058, 3 pages, (Jul. 9, 2010).

* cited by examiner

*Primary Examiner* — Richard Schnizer
*Assistant Examiner* — Audrea Buckley
(74) *Attorney, Agent, or Firm* — Browdy and Neimark, PLLC

(57) ABSTRACT

Disclosed are novel active substance combinations comprising specific heterocyclic trifluorobutenyls and previously known fungicidal agents. Said active substance combinations have a very good synergistic fungicidal, nematicidal, insecticidal, and/or acaricidal effect.

7 Claims, No Drawings

ACTIVE SUBSTANCE COMBINATIONS THAT HAVE NEMATICIDAL, INSECTICIDAL, AND FUNGICIDAL PROPERTIES AND ARE BASED ON TRIFLUOROBUTENYL COMPOUNDS

This application is a 35 U.S.C. §371 U.S. National Phase filing of International Application No. PCT/EP2004/004165, filed Apr. 20, 2004, which claims the benefit of German Patent Application No. 103 19 591.2, filed May 2, 2003.

The present invention relates to novel active compound combinations comprising, firstly, known heterocyclic trifluorobutenyles and, secondly, known fungicidally active compounds, which combinations are highly suitable for controlling animal pests, such as insects and nematodes, and for controlling fungi.

It is already known that certain heterocyclic trifluorobutenyls have nematicidal properties (WO 01/02378 A1). An action of these compounds against insects or fungi has not been reported.

Furthermore, it is known that numerous azole derivatives, aromatic carboxylic acid derivatives, morpholine compounds and other heterocycles can be used for controlling fungi (cf. K. H. Büchel "Pflanzenschutz und Schädlingsbekämpfung" [Crop protection and pest control], pages 87, 136, 141 and 146 to 153, Georg Thieme Verlag, Stuttgart 1977; C. D. S. Thomlin (Editor): "The Pesticide Manual", Eleventh Edition, British Corp Protection Council, Farnham, Surrey, 1997). However, the activity of the compounds in question at low application rates and/or with respect to their spectrum is not always satisfactory.

It has now been found that active compound combinations comprising heterocyclic trifluorobutenyls of the formula (I)

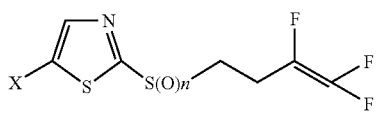

in which
X represents halogen and
n represents 0, 1 or 2,
("active compounds of group 1"),
and
at least one active compound from the following classes of fungicides,
aliphatic, nitrogen-containing fungicides: butylamine, cymoxanil, dodicin, dodine, guazatine, iminoctadine;
amides: carpropamid, chloraniformethan, clozylacon, cyazofamid, cyflufenamid, diclocymet, ethaboxam, fenoxanil, flumetover, furametpyr, prochloraz, quinazamid, silthiofam, triforine, amino acids, such as, for example, benalaxyl, benalaxyl-M furalaxyl, metalaxyl, metalaxyl-M, pefurazoate, benzamides, such as, for example, benzohydroxamic acid, tioxymid, trichlamide, tricyclamide, zarilamid, zoxamide, furamides, such as, for example, cyclafuramid, furmecyclox, phenylsulfamides, such as, for example, dichlofluanid, tolylfluanid, valinamides, such as, for example, benthiavalicarb, iprovalicarb, anilides, such as, for example, benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide, thiadinil, benzanilides, such as, for example, benodanil, flutolanil, mebenil, mepronil, salicylanilide, tecloftalam, furanilides, such as, for example, fenfuram, furalaxyl, furcarbanil, methfuroxam, sulfonanilides, such as, for example, flusulfamide;
antibiotic fungicides: aureofungin, blasticidin-S, capsimycin, cycloheximide, griseofulvin, irumamycin, kasugamycin, mildiomycin, natamycin, polyoxins, polyoxorim, streptomycin, validamycin, strobins, such as, for example, azoxystrobin, dimoxystrobin, fluoxastrobin, kresoximmethyl, metominostrobin, orysastrobin, picoxystrobin, pyraclostrobin, trifloxystrobin;
aromatic fungicides: biphenyl, chloroneb, chlorothalonil, cresol, dicloran, hexachlorobenzene, pentachlorophenol, quintozene, sodium pentachlorophenoxide, tecnazene;
benzimidazoles: benomyl, carbendazim, chlorfenazole, cypendazole, debacarb, fuberidazole, mecarbinzid, rabenzazole, thiabendazole;
benzothiazoles: bentaluron, chlobenthiazone, TCMTB;
diphenyl fungicides: bithionol, dichlorophen, diphenylamine;
carbamates: benthiavalicarb, furophanate, iprovalicarb, propamocarb, thiophanate, thiophanate-methyl, benzimidazolylcarbamate, such as, for example, benomyl, carbendazim, cypendazole, debacarb, mecarbinzid, carbanilates, such as, for example, diethofencarb;
conazoles: conazoles (imidazoles), such as, for example, climbazole, clotrimazole, imazalil, oxpoconazole, prochloraz, triflumizole, conazoles (triazoles), such as, for example, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P;
copper fungicides: Bordeaux mixture, Burgundy mixture, Cheshunt mixture, copper acetate, copper carbonate (basic), copper hydroxide, copper naphthenate, copper oleate, copper oxychloride, copper sulfate, copper sulfate (basic), copper zinc chromate, cufraneb, cuprobam, cuprous oxide, mancopper, oxine copper;
dicarboximides: famoxadone, fluoroimide, dichlorophenyl-dicarboximides, such as, for example, chlozolinate, dichlozoline, iprodione, isovaledione, myclozolin, procymidone, vinclozolin, phthalimides, such as, for example, captafol, captan, ditalimfos, folpet, thiochlorfenphim;
dinitrophenols: binapacryl, dinobuton, dinocap, dinocap-4, dinocap-6, dinocton, dinopenton, dinosulfon, dinoterbon, DNOC;
dithiocarbamates: azithiram, carbamorph, cufraneb, cuprobam, disulfiram, ferbam, metam, nabam, tecoram, thiram, ziram, cyclic dithiocarbamates, such as, for example, dazomet, etem, milneb, polymeric dithiocarbamates, such as, for example, mancopper, mancozeb, maneb, metiram, polycarbamate, propineb, zineb;
imidazoles: cyazofamid, fenamidone, fenapanil, glyodin, iprodione, isovaledione, pefurazoate, triazoxide, (see also: conazoles (imidazoles));
morpholines: aldimorph, benzamorf, carbamorph, dimethomorph, dodemorph, fenpropimorph, flumorph, tridemorph;
organophosphorus fungicides: ampropylfos, ditalimfos, edifenphos, fosetyl, hexylthiofos, iprobenfos, phosdiphen, pyrazophos, tolclofos-methyl, triamiphos;
organotin compounds: decafentin, fentin, tributyltin oxide;
oxathiines: carboxin, oxycarboxin, oxyfenthiin;

oxazoles: chlozolinate, dichlozoline, drazoxolon, famoxadone, hymexazol, metazoxolon, myclozolin, oxadixyl, vinclozolin;
pyridines: boscalid, buthiobate, dipyrithione, fluazinam, pyridinitril, pyrifenox, pyroxychlor, pyroxyfur;
pyrimidines: andoprim, bupirimate, cyprodinil, diflumetorim, dimethirimol, ethirimol, fenarimol, ferimzone, meferimzone, mepanipyrim, nuarimol, pyrimethanil, triarimol;
pyrroles: fenpiclonil, fludioxonil, fluoroimide, pyrrolnitrine;
quinolines: ethoxyquin, halacrinate, 8-hydroxyquinoline sulfate, quinacetol, quinoxyfen;
quinones: benquinox, chloranil, dichlone, dithianon;
quinoxalines: chinomethionat, chlorquinox, thioquinox;
thiazoles: ethaboxam, etridiazole, metsulfovax, octhilinone, thiabendazole, thiadifluor, thifluzamide;
thiocarbamates: methasulfocarb, prothiocarb;
thiophenes: ethaboxam, silthiofam;
triazines: anilazine;
triazoles: bitertanol, fluotrimazole, triazbutil (see also conazoles (triazoles));
ureas: bentaluron, pencycuron, quinazamid;
non-classified fungicides: acibenzolar, acypetacs, allyl alcohol, benzalkonium chloride, benzamacril, bethoxazin, carvone, chloropicrin, cyprofuram, DBCP, dehydroacetic acid, diclomezine, diethylpyrocarbonate, fenaminosulf, fenitropan, fenpropidin, formaldehyde, hexachlorobutadiene, isoprothiolane, methylbromid, methyl isothiocyanate, metrafenone, nicobifen, nitrostyrene, nitrothal-isopropyl, OCH, oxolinix acid, 2-phenylphenol, phthalide, piperalin, probenazole, proquinazid, pyroquilon, sodium orthophenylphenoxide, spiroxamine, sultropen, thicyofen, tricyclazole, zinc naphthenate, (2S)—N—[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridincarboxamide; 3,4,5-trichloro-2,6-pyridinedicarbonitrile; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decan-3-amine;

("active compounds of group 2")
have very good nematicidal, insecticidal and/or fungicidal properties.

Surprisingly, the nematicidal, fungicidal and/or insecticidal action of the active compound combination according to the invention is considerably higher than the sum of the actions of the individual active compounds. A true unforeseeable synergistic effect is present, and not just an addition of actions.

In addition to at least one active compound of the formula (I), the active compound combinations according to the invention comprise at least one active compound of group 2.

Preference is given to active compound combinations as described above which, as active compound of group 1, comprise at least one compound of the formula (I) in which
X represents fluorine, chlorine or bromine and
n represents 0 or 2.

Particular preference is furthermore given to active compound combinations as described above which, as active compound of group 1, comprise at least one compound of the formula (I) in which
X represents fluorine or chlorine and
n represents 2.

The present invention provides in particular active compound combinations as described above which, in addition to at least one active compound from group 1 according to one of the above definitions, comprise at least one active compound of group 2 from one of the following above-defined classes of fungicides: amides, strobins, conazoles, dicarboximides, organophosphorus fungicides, carbamates and urea derivatives.

Especially preferred are active compound combinations as described above which comprise a compound of the formula (IA) according to the above-defined active compounds of group 1

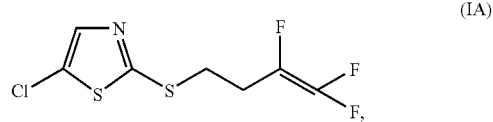

(IA)

or a compound of the formula (IB) according to the above-defined active compounds of group 1

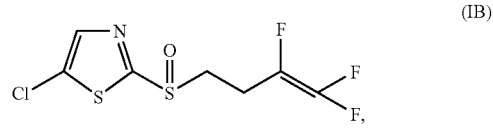

(IB)

or a compound of the formula (IC) according to the above-defined active compounds of group 1

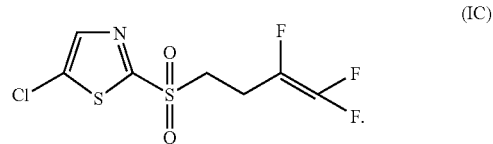 [SMILES: O=S(=O)(CCC(F)=C(F)F)c1ncc(Cl)s1]

(IC)

Preference is given to active compound combinations of in each case one of the active compounds of the formula (IA), (IB) or (IC), and in each case one of the following active compounds from the class of the amides, strobins, conazoles, dicarboximides, organophosphorus fungicides, carbamates or urea derivatives:
tolylfluanid, carpropamid, chloraniformethan, clozylacon, cyazofamid, cyflufenamid, diclocymet, ethaboxam, fenoxanil, flumetover, furametpyr, prochloraz, quinazamid, silthiofam, triforine, benalaxyl, benalaxyl-M, furalaxyl, metalaxyl, metalaxyl-M, pefurazoate, benzohydroxamic acid, tioxymid, trichlamide, tricyclamide, zarilamid, zoxamide, cyclafuramid, furmecyclox, dichlofluanid, benthiavalicarb, iprovalicarb, benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide, tiadinil, benzanilides, such as, for example, benodanil, flutolanil, mebenil, mepronil, salicylanilide, tecloftalam; furanilides, such as, for example, fenfuram, furalaxyl, furcarbanil, methfuroxam, flusulfamide ("amides");

trifloxystrobin, fluoxastrobin, azoxystrobin, dimoxystrobin, kresoxim-methyl, metominostrobin, orysastrobin, picoxystrobin, pyraclostrobin, ("strobins");

tebuconazole, prothioconazole, prochloraz, climbazole, clotrimazole, imazalil, oxpoconazole, triflumizole, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, quinconazole, simeconazole, tetraconazole, triadimefon, triadimenol, triticonazole, uniconazole, uniconazole-P ("conazoles");

iprodione, famoxadone, fluoroimide, chlozolinate, dichlozoline, isovaledione, myclozolin, procymidone, vinclozolin, captafol, captan, ditalimfos, folpet, thiochlorfenphim ("dicarboximides");

fosetyl, ampropylfos, ditalimfos, edifenphos, hexylthiofos, iprobenfos, phosdiphen, pyrazophos, tolclofos-methyl, triamiphos ("organophosphorus fungicides");

benthiavalicarb, furophanate, iprovalicarb, propamocarb, thiophanate, thiophanate-methyl, benomyl, carbendazim, cypendazole, debacarb, mecarbinzid, diethofencarb ("carbamates");

pencycuron, bentaluron, quinazamid ("ureas"), or one of the active compounds hymexazole (an oxazole) or fludioxonil (a pyrrole).

Especially preferred are active compound combinations comprising an active compound of the formula (IC) (active compounds of group 1) and one of the following active compounds from the class of the amides, strobins, conazoles, dicarboximides, organophosphorus fungicides or urea derivatives:

tolylfluanid, carpropamid, chloraniformethan, clozylacon, cyazofamid, cyflufenamid, diclocymet, ethaboxam, fenoxanil, flumetover, furametpyr, prochloraz, quinazamid, silthiofam, triforine, benalaxyl, benalaxyl-M, furalaxyl, metalaxyl, metalaxyl-M, pefurazoate, benzohydroxamic acid, tioxymid, trichlamide, tricyclamide, zarilamid, zoxamide, cyclafuramid, furmecyclox, dichlofluanid, benthiavalicarb, iprovalicarb, benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide, tiadinil, benzanilides, such as, for example, benodanil, flutolanil, mebenil, mepronil, salicylanilide, tecloftalam; furanilides, such as, for example, fenfuram, furalaxyl, furcarbanil, methfuroxam, flusulfamide ("amides");

trifloxystrobin, fluoxastrobin, azoxystrobin, dimoxystrobin, kresoxim-methyl, metominostrobin, orysastrobin, picoxystrobin, pyraclostrobin ("strobins");

tebuconazole, prochloraz, climbazole, clotrimazole imazalil, oxpoconazole, triflumizole, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tetraconazole, triadimefon, triadimenol, triticonazole, uniconazole, uniconazole-P ("conazoles");

iprodione, famoxadone, fluoroimide, chlozolinate, dichlozoline, isovaledione, myclozolin, procymidone, vinclozolin, captafol, captan, ditalimfos, folpet, thiochlorfenphim ("dicarboximides");

fosetyl, ampropylfos, ditalimfos, edifenphos, hexylthiofos, iprobenfos, phosdiphen, pyrazophos, tolclofos-methyl, triamiphos ("organophosphorus fungicides");

pencycuron, bentaluron, quinazamid ("ureas"), or one of the active compounds hymexazole or fludioxonil.

From among the abovementioned preferred class of the conazoles, in turn, the triazoles are of particular interest. From among the abovementioned preferred class of the dicarboximides, in turn, the dichlorophenyldicarboximides are of particular interest.

Particularly preferred combinations according to the invention are shown in the table below.

| Active compound of group 1 | Active compound of group 2 |
|---|---|
| (IA) | fluoxastrobin |

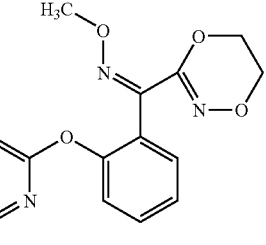

| (IB) | fluoxastrobin |
| (IC) | fluoxastrobin |
| (IA) | fosetyl-Al |

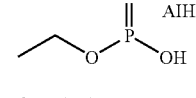

| (IB) | fosteyl-Al |
| (IC) | fosetyl-Al |
| (IA) | fludioxonil |

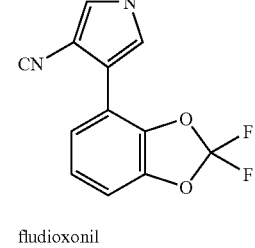

| (IB) | fludioxonil |
| (IC) | fludioxonil |
| (IA) | iprodione |

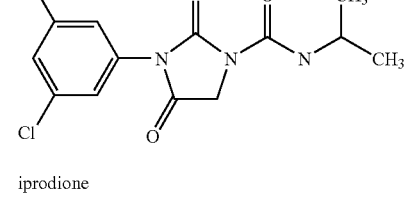

| (IB) | iprodione |
| (IC) | iprodione |

| Active compound of group 1 | Active compound of group 2 |
|---|---|
| (IA) | pencycuron |

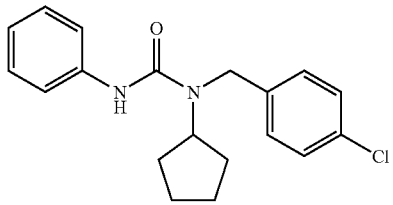 [SMILES: O=C(Nc1ccccc1)N(Cc1ccc(Cl)cc1)C1CCCC1]

| | |
|---|---|
| (IB) | pencycuron |
| (IC) | pencycuron |
| (IA) | prochloraz |

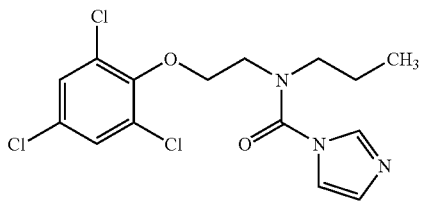 [SMILES: CCCN(CCOc1c(Cl)cc(Cl)cc1Cl)C(=O)n1ccnc1]

| | |
|---|---|
| (IB) | prochloraz |
| (IC) | prochloraz |
| (IA) | prothioconazole |

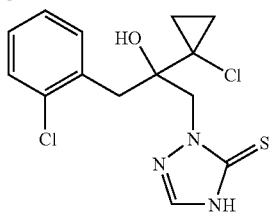 [SMILES: OC(Cc1ccccc1Cl)(Cn1nc[nH]c1=S)C1(Cl)CC1]

| | |
|---|---|
| (IB) | prothioconazole |
| (IC) | prothioconazole |
| (IA) | tebuconazole |

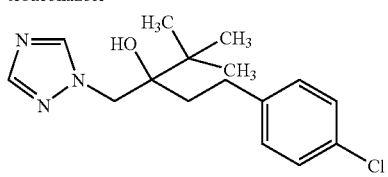

| | |
|---|---|
| (IB) | tebuconazole |
| (IC) | tebuconazole |
| (IA) | tolylfluanid |

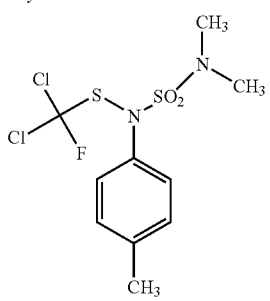

| | |
|---|---|
| (IB) | tolylfluanid |
| (IC) | tolylfluanid |

| Active compound of group 1 | Active compound of group 2 |
|---|---|
| (IA) | trifloxystrobin |

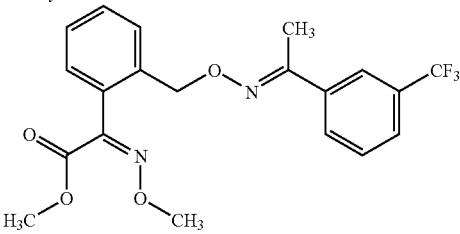

| | |
|---|---|
| (IB) | trifloxystrobin |
| (IC) | trifloxystrobin |

In addition, the active compound combinations may also comprise other fungicidally, acaricidally or insecticidally active components which may be admixed.

If the active compounds are present in the active compound combinations according to the invention in certain weight ratios, the synergistic effect is particularly pronounced. However, the weight ratios of the active compounds in the active compound combinations may be varied within a relatively wide range. In general, the combinations according to the invention comprise active compounds of the formula (I) and a co-component from group 2 in the preferred and particularly preferred mixing ratios given in an exemplary manner in the table below:

the mixing ratios are based on weight ratios. The ratio is to be understood as meaning active compound of the formula (I): co-component

TABLE 2

| Co-component | Preferred mixing ratio | Particularly preferred mixing ratio |
|---|---|---|
| fluquinconazol | 1000:1 to 1:5 | 500:1 to 1:1 |
| tebuconazol | 1000:1 to 1:5 | 500:1 to 1:1 |
| bitertanol | 1000:1 to 1:5 | 500:1 to 1:1 |
| triadimenol | 1000:1 to 1:5 | 500:1 to 1:1 |
| triadimefon | 1000:1 to 1:5 | 500:1 to 1:1 |
| difenoconazol | 1000:1 to 1:5 | 500:1 to 1:1 |
| flusilazol | 1000:1 to 1:5 | 500:1 to 1:1 |
| prochloraz | 1000:1 to 1:5 | 500:1 to 1:1 |
| penconazol | 1000:1 to 1:5 | 500:1 to 1:1 |
| 2-(1-chlorocyclopropyl)-1-(2-chlorophenyl)-3-(5-mercapto-1,2,4-triazol-1-yl)propan-2-ol | 1000:1 to 1:5 | 500:1 to 1:1 |
| kresoximmethyl | 1000:1 to 1:5 | 500:1 to 1:1 |
| azoxystrobin | 1000:1 to 1:5 | 500:1 to 1:1 |
| trifloxystrobin | 1000:1 to 1:5 | 500:1 to 1:1 |
| picoxystrobin | 1000:1 to 1:5 | 500:1 to 1:1 |
| 3-{1-[4-<2-chlorophenoxy>-5-fluoropyrimid-6-yloxy)phenyl]-1-(methoxyimino)methyl}-5,6-dihydro-1,4,2-dioxazine | 1000:1 to 1:5 | 500:1 to 1:1 |
| maneb | 100:1 to 1:10 | 50:1 to 1:1 |
| propineb | 100:1 to 1:10 | 50:1 to 1:1 |
| mancozeb | 100:1 to 1:10 | 50:1 to 1:1 |
| captan | 100:1 to 1:10 | 50:1 to 1:1 |
| folpet (Phaltan) | 100:1 to 1:10 | 50:1 to 1:1 |
| dichlofluanid | 200:1 to 1:10 | 100:1 to 1:2 |
| tolylfluanid | 200:1 to 1:10 | 100:1 to 1:2 |
| famoxadon | 100:1 to 1:10 | 50:1 to 1:1 |
| fenamidon | 100:1 to 1:10 | 50:1 to 1:1 |
| carpropamid | 100:1 to 1:10 | 50:1 to 1:1 |
| iprovalicarb | 100:1 to 1:10 | 50:1 to 1:1 |
| procymidon | 100:1 to 1:10 | 50:1 to 1:1 |

TABLE 2-continued

| Co-component | Preferred mixing ratio | Particularly preferred mixing ratio |
| --- | --- | --- |
| vinclozolin | 100:1 to 1:10 | 50:1 to 1:1 |
| iprodion | 100:1 to 1:10 | 50:1 to 1:1 |
| cyprodinil | 100:1 to 1:10 | 50:1 to 1:1 |
| cyamidazosulfamid | 100:1 to 1:10 | 50:1 to 1:1 |
| 1-(3,5-dimethylisoxazole-4-sulfonyl)-2-chloro-6,6-difluoro-[1,3]-dioxolo-[4,5f]benzimidazole | 100:1 to 1:10 | 50:1 to 1 1 |
| pyrimethanil | 100:1 to 1:10 | 50:1 to 1:1 |
| mepanipyrim | 100:1 to 1:10 | 50:1 to 1:1 |
| spiroxamin | 100:1 to 1:10 | 50:1 to 1:1 |
| chlorothalonil | 1000:1 to 1:5 | 500:1 to 1:1 |
| iminoctadien-triacetate | 1000:1 to 1:5 | 500:1 to 1:1 |
| fludioxonil | 1000:1 to 1:5 | 500:1 to 1:1 |
| acibenzolar-s-methyl (Bion) | 1000:1 to 1:5 | 500:1 to 1:1 |
| dimetomorph | 1000:1 to 1:5 | 500:1 to 1:1 |
| cymoxanil | 1000:1 to 1:5 | 500:1 to 1:1 |
| fosetyl-al | 1000:1 to 1:5 | 500:1 to 1:1 |
| pencycuron | 1000:1 to 1:5 | 500:1 to 1:1 |
| fenhexamid | 1000:1 to 1:5 | 500:1 to 1:1 |
| zoxamid | 1000:1 to 1:5 | 500:1 to 1:1 |
| carbendazim | 1000:1 to 1:5 | 500:1 to 1:1 |
| rabcide | 1000:1 to 1:5 | 500:1 to 1:1 |
| coratop | 200:1 to 1:10 | 100:1 to 1:2 |
| chinomethionat | 200:1 to 1:10 | 100:1 to 1:2 |
| fluazinam | 100:1 to 1:10 | 50:1 to 1:1 |
| metalaxyl-M | 100:1 to 1:10 | 50:1 to 1:1 |
| sulfur | 100:1 to 1:100 | 10:1 to 1:10 |
| copper | 100:1 to 1:100 | 10:1 to 1:10 |

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal and bacterial diseases which come under the generic names listed above are mentioned as examples, but not by way of limitation:

*Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*; *Pythium* species, such as, for example, *Pythium ultimum*; *Phytophthora* species, such as, for example, *Phytophthora infestans*; *Pseudoperonospora* species, such as, for example, *Pseudoperonospora humuli* or *Pseudoperonospora cubensis*; *Plasmopara* species, such as, for example, *Plasmopara viticola*; *Bremia* species, such as, for example, *Bremia lactucae*; *Peronospora* species, such as, for example, *Peronospora pisi* or *P. brassicae*; *Erysiphe* species, such as, for example, *Erysiphe graminis*; *Sphaerotheca* species, such as, for example, *Sphaerotheca fuliginea*; *Podosphaera* species, such as, for example, *Podosphaera leucotricha*; *Venturia* species, such as, for example, *Venturia inaequalis*; *Pyrenophora* species, such as, for example, *Pyrenophora teres* or *P. graminea* (conidia form: Drechslera, syn: Helminthosporium); *Cochliobolus* species, such as, for example, *Cochliobolus sativus* (conidia form: Drechslera, syn: Helminthosporium); *Uromyces* species, such as, for example, *Uromyces appendiculatus*; *Puccinia* species, such as, for example, *Puccinia recondita*; *Sclerotinia* species, such as, for example, *Sclerotinia sclerotiorum*; *Tilletia* species, such as, for example, *Tilletia caries*; *Ustilago* species, such as, for example, *Ustilago nuda* or *Ustilago avenae*; *Pellicularia* species, such as, for example, *Pellicularia sasakii*; *Pyricularia* species, such as, for example, *Pyricularia oryzae*; *Fusarium* species, such as, for example, *Fusarium culmorum*; *Botrytis* species, such as, for example, *Botrytis cinerea*; *Septoria* species, such as, for example, *Septoria nodorum*; *Leptosphaeria* species, such as, for example, *Leptosphaeria nodorum*; *Cercospora* species, such as, for example, *Cercospora canescens*; *Alternaria* species, such as, for example, *Alternaria brassicae*; and *Pseudocercosporella* species, such as, for example, *Pseudocercosporella herpotrichoides*.

The fact that the active compound combinations are well tolerated by plants at the concentrations required for controlling plant diseases permits the treatment of above-ground parts of plants, of propagation stock and seeds, and of the soil.

The active compound combinations according to the invention are also suitable for increasing the yield of crops. Moreover, they have reduced toxicity and are tolerated well by plants.

In the protection of materials, the active compound combinations according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compound combinations according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compound combinations according to the invention preferably act against fungi, in particular molds, wood-discoloring and wood-destroying fungi (Basidiomycetes), and against slime organisms and algae.

Microorganisms of the following genera may be mentioned as examples:

*Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, such as *Escherichia coli*, *Pseudomonas*, such as *Pseudomonas aeruginosa*, and *Staphylococcus*, such as *Staphylococcus aureus*.

Depending on their particular physical and/or chemical properties, the active compound combinations can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compound combinations can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compound combinations according to the invention as fungicides, the application rates can be varied within a relatively wide range, depending on the kind of application. For the treatment of parts of plants, the active compound application rates are generally between 0.1 and 10000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The compositions used for protecting industrial materials comprise the active compounds generally in an amount of from 1 to 95% by weight, preferably from 10 to 75% by weight.

The use concentrations of the active compound combinations according to the invention depend on the nature and occurrence of the microorganisms to be controlled and on the composition of the material to be protected. The optimum amount employed can be determined by a series of tests. In general, the use concentrations are in the range from 0.001 to 5% by weight, preferably from 0.05 to 1.0% by weight, based on the material to be protected.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeder's certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

A synergistic effect in fungicides, nematicides, insecticides and acaricides is always present when the fungicidal, nematicidal, insecticidal and/or acaricidal action of the active compound combinations exceeds the total of the actions of the active compounds when applied individually.

The expected action for a given combination of two active compounds can be calculated as follows (cf. Colby, S. R., "Calculating Synergistic and Antagonistic Responses of Herbicide Combinations", Weeds 15 (1967), 20-22):

If

X is the efficacy or kill rate, expressed as a percentage of the untreated control, when employing active compound A in a concentration of m ppm, Y is the efficacy or kill rate, expressed as a percentage of the untreated control, when employing active compound B in a concentration of m ppm and E is the efficacy or kill rate, expressed as a percentage of the untreated control, when employing active compounds A and B in a concentration of m and n ppm, then $$E = X + Y - \frac{X \cdot Y}{100}.$$

If the actual fungicidal or nematicidal, insecticidal and/or acaricidal action exceeds the calculated value, the action of the combination is superadditive, i.e. a synergistic effect is present. In this case, the actually observed efficacy or kill rate must exceed the value calculated using the above formula for the expected efficacy (E).

EXAMPLES

Example A

Meloidogyne Test (Nematicidal Action)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and plants develop. On the roots, galls are formed.

After the desired period of time, the nematicidal action is determined in % by the formation of galls. 100% means that no galls have been found; 0% means that the number of galls on the treated plants corresponds to that of the untreated control. The determined kill rates are inserted into Colby's formula.

In this test, the following active compound combinations according to the present application showed a synergistically enhanced activity compared to the active compounds applied on their own (found*=activity found in the test; calc.**=activity calculated according to Colby):

TABLE 3

| | (IC) + prothioconazole | |
|---|---|---|
| Active compound | Active compound concentration [ppm] | Kill rate [%] after 14 days |
| (IC) | 0.8 | 50 |
| prothioconazole | 20 | 50 |
| (IC) + prothioconazole (1:25) | 0.8 + 20 | found*: 80 calc.**: 75 |

TABLE 4

| | (IC) + fludioxonil | |
|---|---|---|
| Active compound | Active compound concentration [ppm] | Kill rate [%] after 14 days |
| (IC) | 0.8 | 50 |
| fludioxonil | 20 | 0 |
| (IC) + fludioxonil (1:25) | 0.8 + 20 | found*: 90 calc.**: 50 |

TABLE 5

| | (IC) + trifloxystrobin | |
|---|---|---|
| Active compound | Active compound concentration [ppm] | Kill rate [%] after 14 days |
| (IC) | 0.8 | 50 |
| trifloxystrobin | 20 | 0 |
| (IC) + trifloxystrobin (1:25) | 0.8 + 20 | found*: 60 calc.**: 50 |

Example B

Plutella Test, Sensitive Strain (Insecticidal Action)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moth (*Plutella xylostella*, sensitive strain) while the leaves are still moist. After the desired period of time, the kill in % is determined. 100% means that all caterpillars have been killed; 0% means that none of the caterpillars have been killed. The determined kill rates are inserted into Colby's formula.

In this test, the following active compound combination in accordance with the present application showed a synergistically enhanced activity compared to the active compounds applied on their own (found*=activity found in the test; calc.**=activity calculated according to Colby):

TABLE 6

| | (IC) + trifloxystrobin | |
|---|---|---|
| Active compound | Active compound concentration [ppm] | Kill rate [%] after 3 days |
| (IC) | 100 | 0 |
| trifloxystrobin | 100 | 15 |
| (IC) + trifloxystrobin (1:1) | 100 + 100 | found*: 55 calc.**: 15 |

Example C

Mycelium Growth Test

Nutrient medium: 39 parts by weight of potato dextrose agar
5 parts by weight of agar agar These are dissolved in 1000 ml of distilled water and autoclaved at 121° C. for 30 minutes.
Solvent: 49 parts by weight of acetone
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the required stock solution concentration. To establish the test concentration, in each case 1 part by volume of the active compound stock solution is thoroughly mixed with 9 parts by volume of liquid nutrient medium and poured into Petri dishes. Once the nutrient medium has cooled and solidified, the plates are inoculated with the microorganisms listed in the table below and incubated at about 20° C.

Depending on the growth rate of the microorganisms, evaluation is carried out after 2 to 8 days. 0% means an efficacy which corresponds to that of the control, whereas an efficacy of 100% means that no mycelium growth is observed.

The tables below clearly show that the found activity of the active compound combination according to the invention is higher than the calculated activity, i.e. a synergistic effect is present.

TABLE 7 mycelium growth test with *Phytophthora cactorum* (IC) + pencycuron

| Active compound | Active compound concentration in the nutrient medium [ppm] | Efficacy [%] |
|---|---|---|
| (IC) | 100 | 18 |
| pencycuron | 200 | 0 |
| (IC) + pencycuron (1:2) | 100 + 200 | actual efficacy: 58 expected value calculated according to Colby: 18 |

TABLE 8 mycelium growth test with *Phytophthora cactorum* (IC) + fosetyl-Al

| Active compound | Active compound concentration in the nutrient medium [ppm] | Efficacy [%] |
|---|---|---|
| (IC) | 50 | 7 |
| fosetyl-Al | 100 | 34 |
| (IC) + fosetyl-Al (1:2) | 50 + 100 | actual efficacy: 58 expected value calculated according to Colby: 39 |

TABLE 9 mycelium growth test with *Phytophthora cactorum* (IC) + tolylfluanid

| Active compound | Active compound concentration in the nutrient medium [ppm] | Efficacy [%] |
|---|---|---|
| (IC) | 100 | 23 |
| tolylfluanid | 10 | 65 |
| (IC) + tolylfluanid (1:2) | 100 + 10 | actual efficacy: 92 expected value calculated according to Colby: 73 |

TABLE 10 mycelium growth test with *Phytophthora cactorum* (IC) + trifloxystrobin

| Active compound | Active compound concentration in the nutrient medium [ppm] | Efficacy [%] |
|---|---|---|
| (IC) | 100 | 23 |
| trifloxystrobin | 10 | 29 |
| (IC) + trifloxystrobin (10:1) | 100 + 10 | actual efficacy: 65 expected value calculated according to Colby: 45 |

TABLE 11 mycelium growth test with *Phytophthora cactorum* (IC) + fluoxastrobin

| Active compound | Active compound concentration in the nutrient medium [ppm] | Efficacy [%] |
|---|---|---|
| (IC) | 50 | 7 |
| fluoxastrobin | 5 | 28 |
| (IC) + fluoxastrobin (10:1) | 50 + 5 | actual efficacy: 58 expected value calculated according to Colby: 33 |

TABLE 12 mycelium growth test with *Phytophthora cactorum* (IC) + tebuconazole

| Active compound | Active compound concentration in the nutrient medium [ppm] | Efficacy [%] |
|---|---|---|
| (IC) | 100 | 23 |
| tebuconazole | 100 | 12 |
| (IC) + tebuconazole (1:1) | 100 + 100 | actual efficacy: 88 expected value calculated according to Colby: 32 |

TABLE 13 mycelium growth test with *Phytophthora cactorum* (IC) + prochloraz

| Active compound | Active compound concentration in the nutrient medium [ppm] | Efficacy [%] |
|---|---|---|
| (IC) | 100 | 18 |
| prochloraz | 50 | 30 |
| (IC) + prochloraz (2:1) | 100 + 50 | actual efficacy: 85 expected value calculated according to Colby: 43 |

TABLE 14 mycelium growth test with *Fusarium nivale* (IC) + fosetyl-Al

| Active compound | Active compound concentration in the nutrient medium [ppm] | Efficacy [%] |
|---|---|---|
| (IC) | 1 | 15 |
| fosetyl-Al | 10 | 45 |
| (IC) + fosetyl-Al (1:10) | 1 + 10 | actual efficacy: 73 expected value calculated according to Colby: 53 |

TABLE 15 mycelium growth test with *Rhizoctonia solani* (IC) + fosetyl-Al

| Active compound | Active compound concentration in the nutrient medium [ppm] | Efficacy [%] |
|---|---|---|
| (IC) | 1 | 0 |
| fosetyl-Al | 10 | 12 |

TABLE 15-continued mycelium growth test with *Rhizoctonia solani* (IC) + fosetyl-Al

| Active compound | Active compound concentration in the nutrient medium [ppm] | Efficacy [%] |
|---|---|---|
| (IC) + fosetyl-Al (1:10) | 1 + 10 | actual efficacy: 77 expected value calculated according to Colby: 12 |

TABLE 16 mycelium growth test with *Rhizoctonia solani* (IC) + trifloxystrobin

| Active compound | Active compound concentration in the nutrient medium [ppm] | Efficacy [%] |
|---|---|---|
| (IC) | 10 | 49 |
| trifloxystrobin | 1 | 39 |
| (IC) + trifloxystrobin (10:1) | 10 + 1 | actual efficacy: 86 expected value calculated according to Colby: 69 |

TABLE 17 mycelium growth test with *Rhizoctonia solani* (IC) + fluoxastrobin

| Active compound | Active compound concentration in the nutrient medium [ppm] | Efficacy [%] |
|---|---|---|
| (IC) | 10 | 49 |
| fluoxastrobin | 1 | 39 |
| (IC) + fluoxastrobin (10:1) | 10 + 1 | actual efficacy: 80 expected value calculated according to Colby: 69 |

TABLE 18 mycelium growth test with *Phythium ultimum* (IC) + iprodione

| Active compound | Active compound concentration in the nutrient medium [ppm] | Efficacy [%] |
|---|---|---|
| (IC) | 100 | 11 |
| iprodione | 200 | 9 |
| (IC) + iprodione (1:2) | 100 + 200 | actual efficacy: 84 expected value calculated according to Colby: 19 |

TABLE 19 mycelium growth test with *Phythium ultimum* (IC) + tolylfluanid

| Active compound | Active compound concentration in the nutrient medium [ppm] | Efficacy [%] |
|---|---|---|
| (IC) | 100 | 11 |
| tolylfluanid | 10 | 82 |

TABLE 19-continued mycelium growth test with *Phythium ultimum* (IC) + tolylfluanid

| Active compound | Active compound concentration in the nutrient medium [ppm] | Efficacy [%] |
|---|---|---|
| (IC) + tolylfluanid (10:1) | 100 + 10 | actual efficacy: 99 expected value calculated according to Colby: 84 |

TABLE 20 mycelium growth test with *Phythium ultimum* (IC) + fluoxastrobin

| Active compound | Active compound concentration in the nutrient medium [ppm] | Efficacy [%] |
|---|---|---|
| (IC) | 100 | 31 |
| fluoxastrobin | 10 | 74 |
| (IC) + fluoxastrobin (1:2) | 100 + 10 | actual efficacy: 93 expected value calculated according to Colby: 82 |

TABLE 21 mycelium growth test with *Phythium ultimum* (IC) + tebuconazole

| Active compound | Active compound concentration in the nutrient medium [ppm] | Efficacy [%] |
|---|---|---|
| (IC) | 100 | 11 |
| tebuconazole | 100 | 72 |
| (IC) + tebuconazole (1:1) | 100 + 100 | actual efficacy: 86 expected value calculated according to Colby: 75 |

The invention claimed is:

1. A synergistic composition, characterized in that it comprises an active compound combination comprising (a) one or more active compounds of the formula (I)

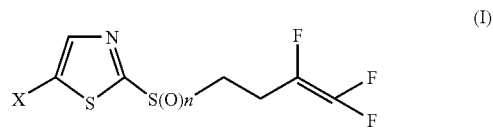

in which

X is halogen and n is 0, 1 or 2, and (b) one or more active compounds prothioconazole, fludioxonil, trifloxystrobin, pencycuron, fosetyl-Al, tolyfluanid, fluoxastrobin, tebuconazole, prochloraz and iprodione.

2. The composition of claim 1, characterized in that it comprises one or more compounds of the formula (I) in which X is fluorine, chlorine, or bromine and n is 0 or 2.

3. The composition of claim 2, characterized in that it comprises one or more compounds of the formula (I) in which X is fluorine or chlorine and n is 2.

4. The composition of claim 1, wherein said one or more active compounds of the formula (I) is one or more of the following compounds of the formulae (IA), (IB) and (IC)

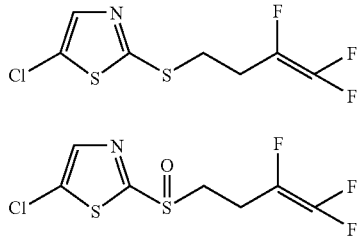

(IA)

(IB)

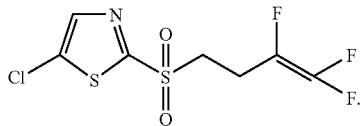

(IC)

5. The composition of claim 4, wherein said one or more active compounds of the formula (I) is a compound of the formula (IC).

6. A method for controlling fungi, nematodes, insects or acarids, wherein the composition of any one of claims 1 to 5 is contacted with nematodes, insects, fungi and/or their habitats.

7. A process for preparing fungicidal, nematicidal, insecticidal and/or fungicidal compositions, characterized in that compositions as claimed in any one of claims 1 to 5 are mixed with extenders and/or surfactants.

* * * * *

UNITED STATES PATENT AND TRADEMARK OFFICE
CERTIFICATE OF CORRECTION

PATENT NO. : 8,426,605 B2  Page 1 of 1
APPLICATION NO. : 10/555106
DATED : April 23, 2013
INVENTOR(S) : Andersch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1227 days.

Signed and Sealed this

Eighth Day of September, 2015

Michelle K. Lee
*Director of the United States Patent and Trademark Office*